United States Patent
Kim

(10) Patent No.: US 6,821,443 B2
(45) Date of Patent: Nov. 23, 2004

(54) PROCESS FOR PRODUCING OZONE-CONTAINING STERILIZING WATER AND AN APPARATUS USED THEREFOR

(76) Inventor: Se-Ham Kim, 102-1703 Howon-Garden Apt., Howon-dong, Uijongbu, Kyungki-do 480-020 (KR)

( * ) Notice: Subject to any disclaimer, the term of this patent is extended or adjusted under 35 U.S.C. 154(b) by 27 days.

(21) Appl. No.: 10/344,297
(22) PCT Filed: Aug. 17, 2001
(86) PCT No.: PCT/KR01/01397
§ 371 (c)(1),
(2), (4) Date: Feb. 7, 2003
(87) PCT Pub. No.: WO02/14226
PCT Pub. Date: Feb. 21, 2002

(65) Prior Publication Data
US 2003/0173309 A1 Sep. 18, 2003

(30) Foreign Application Priority Data
Aug. 18, 2000 (KR) .................................. 2000/23384 U

(51) Int. Cl.$^7$ ................................................. C02F 1/78
(52) U.S. Cl. ............... 210/760; 210/205; 261/DIG. 42; 261/DIG. 75; 422/33
(58) Field of Search ............................. 210/760, 198.1, 210/205; 261/DIG. 42, DIG. 75; 422/28, 29, 33, 186.07

(56) References Cited

U.S. PATENT DOCUMENTS

| 3,719,017 A | * | 3/1973 | Shapiro et al. ................ 53/431 |
| 4,666,480 A | * | 5/1987 | Mann .......................... 62/616 |
| 5,525,242 A | | 6/1996 | Kerecz |
| 6,074,565 A | * | 6/2000 | Buckner ..................... 210/764 |
| 6,488,271 B1 | * | 12/2002 | Nelson et al. ........... 261/121.1 |
| 6,511,525 B2 | * | 1/2003 | Spletzer et al. ................ 95/41 |

FOREIGN PATENT DOCUMENTS

| JP | 10-180270 | 7/1987 |
| JP | 03-056293 | 3/1991 |

* cited by examiner

*Primary Examiner*—Frank M. Lawrence
(74) *Attorney, Agent, or Firm*—Renner, Otto, Boisselle & Sklar, LLP

(57) ABSTRACT

Disclosed is a process for producing ozone-containing sterilizing water and apparatus used in the process. Ozone-containing sterilizing water can be continuously produced by maintaining a mixture of raw water and ozone gas under a predetermined pressure and time with the use of two separate compartments of a compression mix.

27 Claims, 8 Drawing Sheets

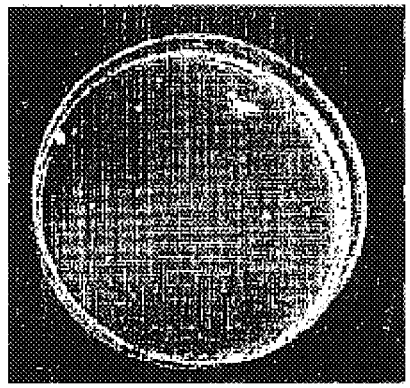

bactericidal effect of ozone-containing water produced by use of general tap water

FIG. 1a

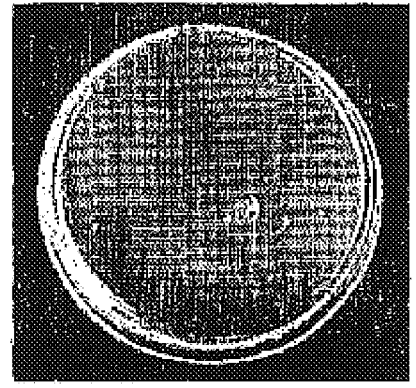

bacter effect of ozone-containing water produced according to a conventional bubble type process

FIG. 1b

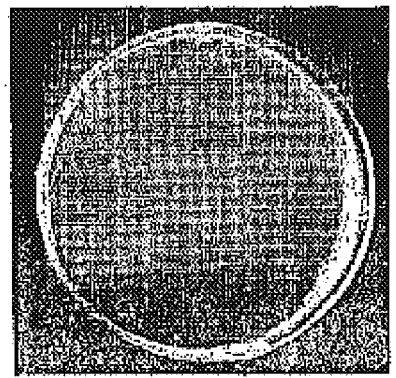

bactericidal effect of ozone-containing water according to the present invention (20kg/cm², 1min)

FIG. 1c

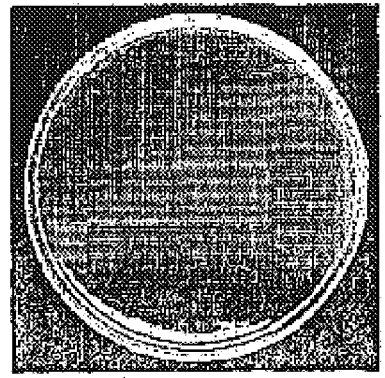

bactericidal effect of ozone-containing water according to the present invention (30kg/cm², 30sec)

FIG. 1d

PROCESS FOR PRODUCING OZONE-CONTAINING STERILIZING WATER AND AN APPARATUS USED THEREFOR

This application is a national phase of International Application No. PCT/KR01/01397 filed Aug. 17, 2001 and published in the English language.

BACKGROUND OF THE INVENTION

1. Field of the Invention

The present invention relates, in general, to a process for producing ozone-containing sterilizing water and apparatus therefor, in particular, to a continuous process for producing ozone-containing sterilizing water used in cleaning/sterilizing various foods or devices in a simple and highly efficient manner and apparatus therefor.

2. Description of the Prior Art

Generally, ozone ($O_3$) has been used in sterilization, bleaching, and oxidization because ozone has strong oxidizing power. Particularly, ozone-containing sterilizing water has been extensively used in food processing or medical fields because no toxic components remain after the cleansing or sterilization therewith.

Ozone-containing sterilizing water is conventionally produced by two processes: a bubble type process, in which ozone gas is added into raw water in the form of bubbles through an ozonizer connected with a vessel holding raw water; and an injector type process, in which ozone gas is added into raw water with the use of a pressure difference resulting from a flow velocity change of raw water passing through a venturi-tube.

However, such bubble type process has problems in that ozone gas added into raw water is not, for the most part, dissolved in raw water, but released from the water surface to the atmosphere, so that low levels of the ozone gas remaining in raw water can perform sterilization only at a low efficiency. What is worse, the released ozone gas is hazardous to humans and causes air pollution.

In the case of the injector type process, since ozone gas is added into raw water with the use of a pressure difference resulting from a flow velocity change of raw water passing through a venturi-tube, solubility of ozone in raw water can be increased but a little to sterilize only the raw water itself. In other words, the ozone concentration prepared by the injector type process is too low to endow raw water with a bactericidal activity.

According to the prior arts, therefore, bacteria in raw water can be killed, but it is impossible to produce ozone-containing sterilizing water with a bactericidal activity, which can sterilize something else other than raw water.

Meanwhile, efforts have been made to overcome the problems and to produce ozone-containing sterilizing water by taking advantage of the solubility increase of ozone gas with the increasing of pressure. For example, the solubility of ozone in raw water is increased by applying pressure into a compression tank into which raw water and zone gas are provided.

However, this method suffers from the problem of being unable to produce ozone-containing water in a continuous type process. That is, ozone-containing sterilizing water can be produced in the quantity as large as the volume of the compression tank in a batch type process, and the production process must be repeated from the beginning stage in order to give ozone-containing sterilizing water in the same amount. The use of huge compression tanks for making a detour around the volume limitation has problems in that the facility and production cost is increased and large amounts of ozone gas should be added into raw water, producing the pollution of the air. Also, the ozone-containing water, although being produced in a sufficient quantity, is disadvantageous in that the ozone gas dissolved therein may be decomposed or released to the atmosphere during storage, thereby reducing a sterilizing efficiency of the ozone-containing water.

Accordingly, there remains a need for providing an apparatus and method that overcome the above problems and can produce ozone-containing sterilizing water continuously and with high efficiency.

SUMMARY OF THE INVENTION

Therefore, it is an object of the present invention to alleviate said problems of the prior arts and to supply an effective, continuous process for producing ozone-containing sterilizing water.

Furthermore, it is another object of the present invention to supply a simple, improved apparatus used in the continuous process for producing ozone-containing sterilizing water.

According to the present invention, there is supplied a process for continuously producing ozone-containing sterilizing water, comprising the steps of: introducing raw water and ozone gas, together, into a compression tank to produce a bubble phase mixture, in which raw water is moved at a faster speed at a predetermined passage to induce a pressure drop, and ozone gas is drawn into the compression tank by the pressure drop; charging bubble phase mixture into any one of compartments of the compression tank, and pressurizing the mixture in the charged compartment to give ozone-containing sterilizing water, in which the compartments are sealably separated by a movable partition within the compression tank; moving the partition to reduce the volume of filled compartment to discharge the ozone-containing sterilizing water while the other compartment is expanded in volume through being charged with the bubble phase mixture; and repeating the above steps.

According to an embodiment of the present invention, raw water and ozone gas are introduced through an injector having a structure with a narrowed cross section therein, raw water is moved at a faster speed at the narrowed cross section to induce a pressure drop, leading to the drawing of the ozone gas into the injector.

Furthermore, the bubble phase mixture is maintained in the compartment for 15 sec to 5 min under a pressure of 15 to 40 $kg/cm^2$, and preferably for 0.5 to 1 min under a pressure of 20 to 30 $kg/cm^2$.

Optionally, the compression tank comprises two compartments divided by a partition, and the partition of the compression tank is a sealably reciprocating piston member. The partition of the compression tank may also be a flexible resilient diaphragm placed in the middle of the compression tank.

According to the present invention, there is supplied an apparatus for continuously producing ozone-containing sterilizing water, comprising a pump for transferring a bubble phase mixture of raw water and ozone gas; and a compression tank, divided into a plurality of compartments, for pressurizing the bubble phase mixture to produce ozone-containing sterilzing water, the plural compartments, in turns, receiving, pressurizing, and discharging the bubble phase mixture.

According to another embodiment of the present invention, the apparatus further comprises an injector for introducing raw water and ozone gas into the compression tank. The injector has a structure with a narrowed cross section therein, such that the raw water is moved at a faster speed at the narrowed cross section to induce a pressure drop, leading to the drawing of the ozone gas into the injector.

Optionally, the compression tank forms a hollow cylinder, comprising a piston member sealably reciprocating within the hollow cylinder; and, a guide bar, extended from the piston to the outside of the compression tank through a hole established in one side of the hollow cylinder, for guiding the motion of the reciprocating piston member, whereby the hollow cylinder is divided into a first compartment and a second compartment by the piston member and the compartments vary in volume according to the motion of the piston member.

The piston member is provided with a plurality of sealing rings at its outer circumference to sealably separate the first and the second compartment from each other so as to prevent the leakage of a fluid pressure exerted on either of the compartments into the other compartment, and the hole is provided with a plurality of sealing rings at its wall to prevent the leakage of a fluid pressure of the compartment to the outside therethrough during the reciprocating motion of the guide bar.

Furthermore, the guide bar allows the piston member to be at a regular position in the hollow cylinder, and is marked on its one side with degrees so that the position of the piston member can be easily seen from outside.

Also, each of the two compartments has an inlet for introducing a bubble phase mixture of raw water and ozone gas, and an outlet for discharging pressurized ozone-containing sterilizing water, wherein a pair of an inlet and an outlet are formed in each of the upper verge and lower verge of the cylinder, respectively.

Optionally, plural compartments are defined by a flexible resilient diaphragm placed in the middle of the compression tank, consisting of a first compartment and a second compartment. The flexible resilient diaphragm is operated in such a way that the flexible resilient diaphragm is expanded toward the second compartment by increasing the pressure of the first compartment to a predetermined value and maintaining the pressure for a predetermined period of time to discharge a fluid from the second compartment, and toward the first compartment by increasing the pressure of the second compartment to a predetermined value and maintaining the pressure for a predetermined period of time to discharge a fluid from the first compartment.

According to the present invention, there is supplied an apparatus for continuously producing ozone-containing sterilizing water, comprising a pump for transferring a bubble phase mixture of raw water and ozone gas; and a cylindrical compression tank, divided into a plurality of compartments by a donut-type piston member having a hole at the center, for pressurizing the bubble phase mixture to produce ozone-containing sterilizing water. The piston member is provided with a plurality of sealing rings at its circumference and at the inner circumference of the hole to sealably separate the plural compartments from each other so as to prevent the leakage of a fluid pressure exerted on either of the compartments into the other compartment, and moving, along a guide bar, in such a reciprocating manner within the compression tank as to pressurize the bubble phase mixture in the plural compartments, in turn. The guide bar extends from one end side of the compression tank to the other side through the hole of the piston member to support the reciprocating motion of the piston member.

According to another embodiment of the present invention, the apparatus further comprises an injector for introducing raw water and ozone gas into the compression tank. The injector has a structure with a narrowed cross section such that the raw water is moved at a faster speed at the narrowed cross section to induce a pressure drop, leading to the drawing of the ozone gas into the injector.

The cylinder further comprises a piston proximity sensor for monitoring the position of the piston within the cylindrical compression tank and determining whether the piston is normally operated or not.

In addition, each of the two compartments has an inlet for introducing a bubble phase mixture of raw water and ozone gas and an outlet for discharging pressurized ozone-containing sterilizing water, wherein a pair of an inlet and an outlet are formed in each of the upper verge and lower verge of the cylinder, respectively.

Furthermore, a backflow prevention check valve is provided just before the inlets for introducing raw water and ozone gas into the injector, each, to prevent the raw water and ozone gas from flowing backward by a back pressure of the pump.

In the present invention, there is supplied an apparatus for continuously producing ozone-containing sterilizing water, comprising an injector for mixing raw water with ozone gas to give a bubble phase mixture of raw water and ozone gas, in which the injector has a structure with a narrowed cross section therein, and the raw water is moved at a faster speed at the narrowed cross section to induce a pressure drop, leading to the drawing of the ozone gas into the injector; a pump for transferring a bubble phase mixture of the raw water and ozone gas; and a compressions tank, formed into a hollow cylinder, for pressurizing the bubble phase mixture to produce ozone-containing sterilizing water, wherein the compression tank comprises a piston member sealably reciprocating within the hollow cylinder; and a guide bar, extended from the piston to the outside of the compression tank through a hole established in one side of the hollow cylinder, for guiding the motion of the reciprocating piston member, whereby the hollow cylinder is divided into a first compartment and a second compartment by the piston member and the compartments vary in volume, in turn, to pressurize the bubble phase mixture according to the reciprocating motion of the piston member.

According to another embodiment of the present invention, the cylinder further comprises a piston proximity sensor for monitoring the position of the piston within the cylindrical compression tank and determining whether the piston is normally operated or not.

Additionally, a backflow prevention check valve is provided just before the inlets for introducing raw water and ozone gas into the injector, respectively, to prevent the raw water and ozone gas from flowing backward by a back pressure of the pump.

According to another embodiment of the present invention, the first and the second compartment are individually provided with an inlet for introducing the bubble phase mixture of ozone gas a raw water thereinto and an outlet for discharging the pressurized ozone-containing sterilizing water therefrom, wherein a pair of an inlet and an outlet are formed in each of the upper verge and lower verge of the cylinder, respectively. The apparatus further comprises a storage tank for storing the ozone-containing sterilizing water, provided with an off-gas filter for venting the gas generated during the storage of the ozone-containing sterilizing in the storage tank; a first conduit, provided with a first solenoid valve, for connecting each outlet with said storage tank; and a second conduit, provided with a second solenoid valve, for connecting each outlet with a drainage pipe.

The first and second solenoid valve function in such a way that, during the trial run of said apparatus, the second solenoid valve is opened with closing of said first solenoid valve so as to drain unpressurized raw water from the compression tank and, during the steady operation of said apparatus, the first solenoid valve is opened with closing of the second solenoid valve so as to discharge ozone-containing sterilizing water into the storage tank.

In the present invention, there is supplied an apparatus for continuously producing ozone-containing sterilizing water, comprising an injector for mixing raw water with ozone gas to give a bubble phase mixture of raw water and ozone gas, in which the injector has a structure with a narrowed cross section therein, and the raw water is moved at a faster speed at the narrowed cross section to induce a pressure drop, leading to the drawing of the ozone gas into the injector; a pump for transferring a bubble phase mixture of the raw water and ozone gas; and a compression tank, formed into a hollow cylinder, for pressurizing the bubble phase mixture to produce ozone-containing sterilizing water, wherein the hollow cylinder is divided into a first and a second compartment by a flexible resilient diaphragm placed in the middle of the compression tank, the flexible resilient diaphragm is operated in such a way that the flexible resilient diaphragm is expanded toward the second compartment by increasing the pressure of the first compartment to a predetermined value and maintaining the pressure for a predetermined period of time to discharge a fluid from the second compartment, and toward the first compartment by increasing the pressure of the second compartment to a predetermined value and maintaining the pressure for a predetermined period of time to discharge a fluid from the first compartment.

According to another embodiment of the present invention, the first land the second compartment are individually provided with an inlet for introducing the bubble phase mixture of ozone gas and raw water thereinto and an outlet for discharging the pressurized ozone-containing sterilizing water therefrom, wherein a pair of an inlet and an outlet are formed in each of the upper verge and lower verge of the cylinder, respectively. The apparatus further comprises a storage tank for storing the ozone-containing sterilizing water, provided with an off-gas filter for venting the gas generated during the storage of the ozone-containing sterilizing in the storage tank; a first conduit, provided with a first solenoid valve, for connecting each outlet with said storage tank; and a second conduit, provided with a second solenoid valve, for connecting each outlet with a drainage pipe.

The first and second solenoid valves function in such a way that, during the trial run of said apparatus, the second solenoid valve is opened with closing of said first solenoid valve so as to drain unpressurized raw water from the compression tank and, during the steady operation of the apparatus, the first solenoid valve is opened with closing of the second solenoid valve so as to discharge ozone-containing sterilizing water into the storage tank.

BRIEF DESCRIPTION OF THE DRAWINGS

The above and other objects, features and other advantages of the present invention will be more clearly understood from the following detailed description taken in conjunction with the accompanying drawings, in which:

FIGS. 1a and 1b are pictures illustrating bactericidal effects of ozone-containing sterilizing water produced by use of general tap water and according to the conventional bubble type process, respectively;

FIGS. 1c and 1d are pictures illustrating bactericidal effects of ozone-containing sterilizing water produced under respective different conditions according to the present invention, respectively;

DETAILED DESCRIPTION OF THE INVENTION

Figure 2:
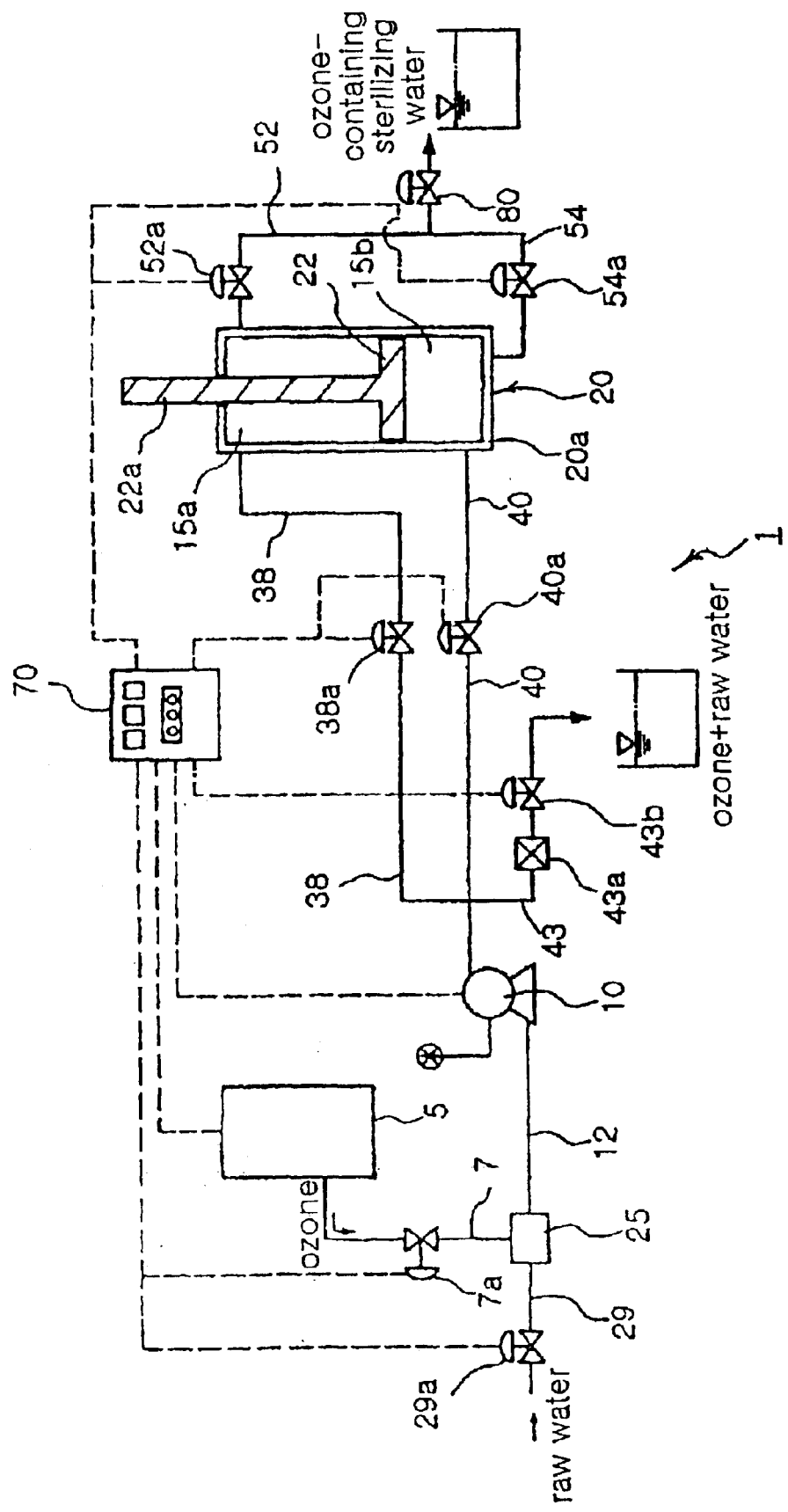
FIG. 2 illustrates a layout of an apparatus used in a process for producing ozone-containing water according to the invention.

A more detailed description will be given of the present invention in conjunction with the following embodiments. The following embodiments are for illustration purposes only and in no way limit the scope of this invention.

In the present invention, ozone gas, which can be generated by use of a conventional ozonizer, is introduced, along with raw water, into an injector and mixed therein. The introduction of the ozone gas is performed by taking advantage of a pressure drop resulting from the fast speed at which the raw water passes into the injector.

For the generation of ozone gas, a conventional ozonizer may be coupled with an oxygen generator which generates oxygen of 95% or higher purity, and operated in a high voltage discharge manner. Use of such highly pure oxygen enjoys the advantage of producing ozone gas in great quantities without concomitant generation of $NO_x$.

Solubility of the generated ozone gas in water under atmospheric pressure is not high (for example, ozone of 0.5 volume per water of 1 volume at 0° C. under 1 atm), such that a part of the ozone gas introduced into the injector is dissolved with the rest of ozone gas existing in the form of bubbles in raw water.

Subsequently, a bubble phase mixture of raw water and ozone gas is pumped into a device used in producing ozone-containing water such as a pressure pump, and maintained under a condition of predetermined pressure and time.

Existing in the form of bubbles in raw water, ozone can be maximally dissolved in raw water under optimum conditions of pressure and time, so that bacteria contained in raw water can be killed, and ozone-containing sterilizing water with a bactericidal activity, which can sterilize something else other than raw water, can be produced.

Ozone-containing sterilizing water produced according to the present invention has better bactericidal activity than that of the prior arts. However, it is observed that the ozone dissolved in the ozone-containing sterilizing water of the present invention is decomposed or released to the atmosphere as time passes. Therefore, the bactericidal activity of the ozone-containing sterilizing water is reduced with increased storage time.

As a result of extensive expecircumferenceents, it was found that, from 20 minutes after its production, the ozone-containing sterilizing water starts to gradually decline in bactericidal activity at room temperature under atmospheric pressure. Accordingly, ozone-containing sterilizing water should be continuously produced at least every 20 minutes.

According to another embodiment of the present invention, ozone-containing sterilizing water can be continuously produced in the process cycle consisting of transferring, pressurizing, maintaining, and discharging, with the use of a compression tank with two compartments, in which two compartments are used in turns.

In detail, raw water and ozone gas are introduced into and mixed together in an injector a manner that, when the raw water passes through a narrowed cross section of the injector, a pressure drop occurs because of its high flow velocity, drawing the ozone gas thereinto.

A bubble phase mixture of raw water and ozone gas from the injector is supplied into any one of two compartments which are separated from each other by a partition reciprocating in a compression tank.

A pressure in a compartment is increased because the bubble phase mixture is supplied into the compartment. After reaching a desired pressure depending on the use of the ozone-containing sterilizing water, the pressure in the compartment should be maintained for such a predetermined time that ozone gas can be dissolved in the maximum quantity in raw water. Then, produced ozone-containing sterilizing water is discharged with concomitant supply of a new bubble phase mixture into the second compartment formed by moving the partition. Accordingly, the pressure in the second compartment is increased to move the partition, which defines the two compartments, toward the first compartment from which the produced ozone-containing sterilizing water is discharged.

Subsequently, the same ozone-containing sterilizing water production process is carried out in the other compartment. That is, the pressure in the second compartment is increased to a desired pressure and maintained for such a predetermined time as to dissolve ozone gas in the maximum quantity in raw water, followed by discharging the ozone-containing sterilizing water thus produced. As such, ozone-containing sterilizing water can be produced in two respective compartments alternately by repeating such process cycles.

In the present invention, the optimum pressure of a bubble phase mixture of raw water and ozone gas in each compartment and the maintenance time of the pressure may vary depending on the ozone concentrations to be obtained, but the bubble phase mixture is preferably maintained for 0.5–5 min under a pressure of 15 to 40 $kg/cm^2$, and more preferably for 0.5–1 min under a pressure of 20 to 30 $kg/cm^2$.

For example, when the pressure is less than 15 $kg/cm^2$, sufficient solubility of ozone gas in raw water cannot be obtained. On the other hand, more than 40 $kg/cm^2$ of the pressure is difficult to maintain, as well as not bringing about further improvement in the solubility of ozone gas in raw water.

Meanwhile, when the pressure is maintained for less than 30 sec, the solubility of ozone gas in raw water cannot reach the maximum. Maintaining the pressure more than 5 min results in decreasing, rather than increasing, the concentration of ozone gas, as well as lengthening the total time period of the process. The concentration decrease is believed to be attributed to the fact that a part of the ozone gas already dissolved in raw water is decomposed or released to the atmosphere.

Maintaining the bubble phase mixture under conditions of predetermined pressure and time in accordance with the present invention, as described above, aids the ozone gas in the bubble phase to be dissolved in maximal quantities in raw water, thereby producing ozone-containing sterilizing water. The resulting ozone-containing sterilizing water can be applied to fields in which a high bactericidal activity is required, such as food processing or medical fields, as well as fields in which a low bactericidal activity is required, such as face-washing water, and also can be used in plant husbandry.

For use in fields requiring a high bactericidal activity, such as food processing or medical fields, the sterilizing water may range, in ozone concentration, from 1.0 to 2.5 ppm. Within the range of 0.2 to 1.0 ppm fall preferable ozone concentrations of the sterilizing water to be applied for face washing or plant husbandry.

Optionally, a partition of a compression tank may be a piston member reciprocating in such a state that each compartment, which is formed by the partition, is sealed tightly in a hollow cylinder; or may be a flexible resilient diaphragm placed in the middle of the compression tank.

Figure 3:
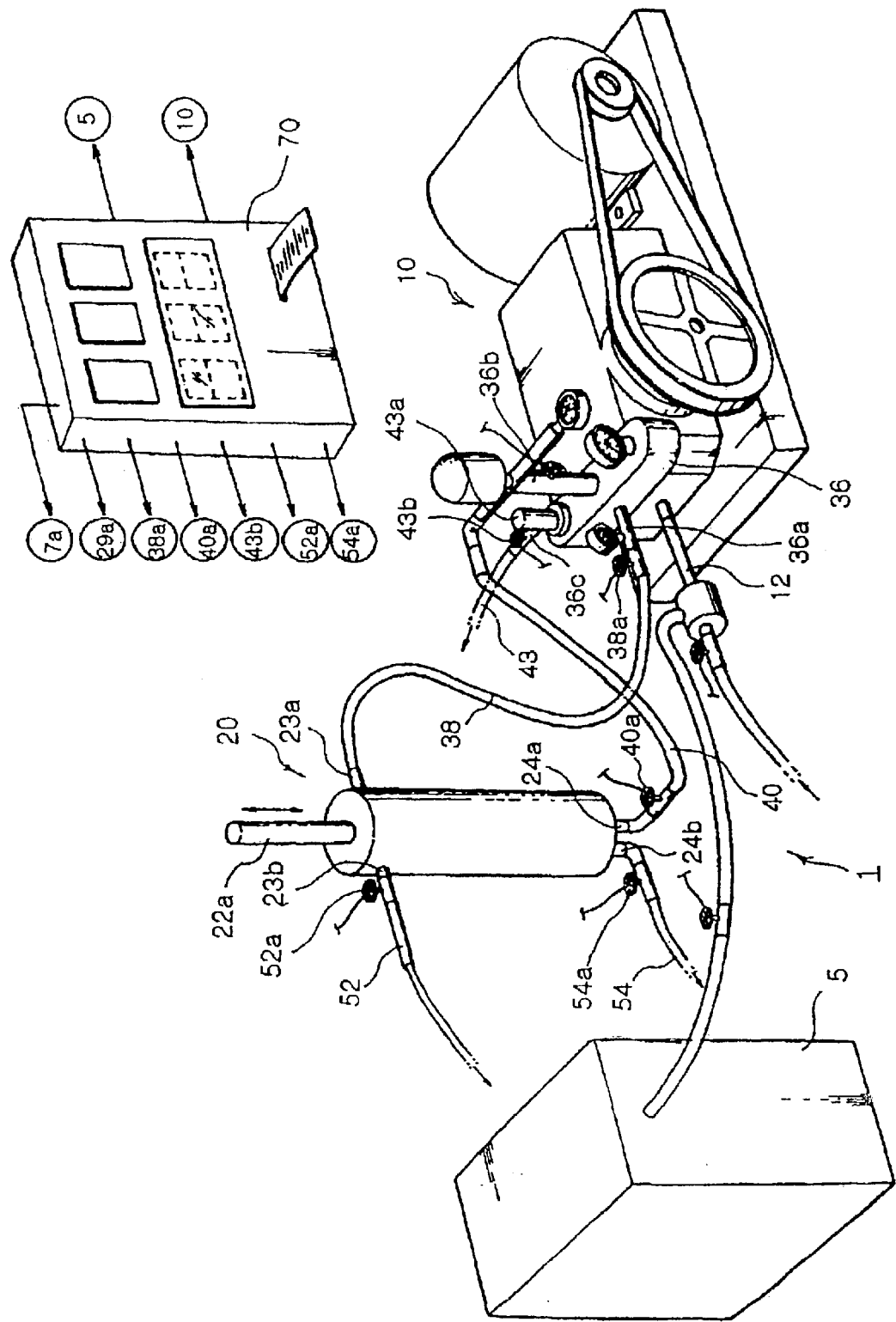
FIG. 3 is a schematic perspective view of an apparatus used in a process for producing ozone-containing water according to the invention.

With reference to FIGS. 2 and 3, then present invention is illustrated in accordance with an aspect. Shown is an apparatus 1 with a simple structure, which is small in size, convenient to use, and capable of producing ozone-containing sterilizing water in a continuous process. The apparatus 1, as shown in FIGS. 2 and 3, comprises a pump 10 for transferring a mixture of ozone gas and raw water under pressure and an ozonizer 5 for generating the ozone gas. Also, the apparatus 1 is provided with a compression tank 20 in which two compartments 15a and 15b receive in turns the bubble phase mixture of ozone gas and raw water supplied from the pump 10. In the apparatus, ozone-containing sterilizing water can be continuously produced by pressurizing in turns respective bubble phase mixtures in two separate compartments 15a and 15b of the compression tank 20.

Continuously generating ozone gas ($O_3$), the ozonizer 5 may be operated in a high voltage discharge type manner. As such, commercially available ozonizers may be useful, for example, Model OZ-2 A220-40, manufactured by Dong Woo Co., Korea, whose capacity is 40 mg/hr at AC 220 V, 60 Hz, at an output voltage of 5 kW. Another example is Pacific Ozone Model, manufactured by ATI, USA, whose capacity is 6 g/hr at AC 220 V, 60 Hz, an output voltage of 180 W.

Ozone gas ($O_3$), which is continuously generated from the ozonizer 5 (or a system for generating ozone) as described above, flows through a pipe 7 and an automatic control valve 7a into an injector 25, into which raw water ($H_2O$) is introduced through a valve 29a and an inlet pipe 29.

Figure 4:
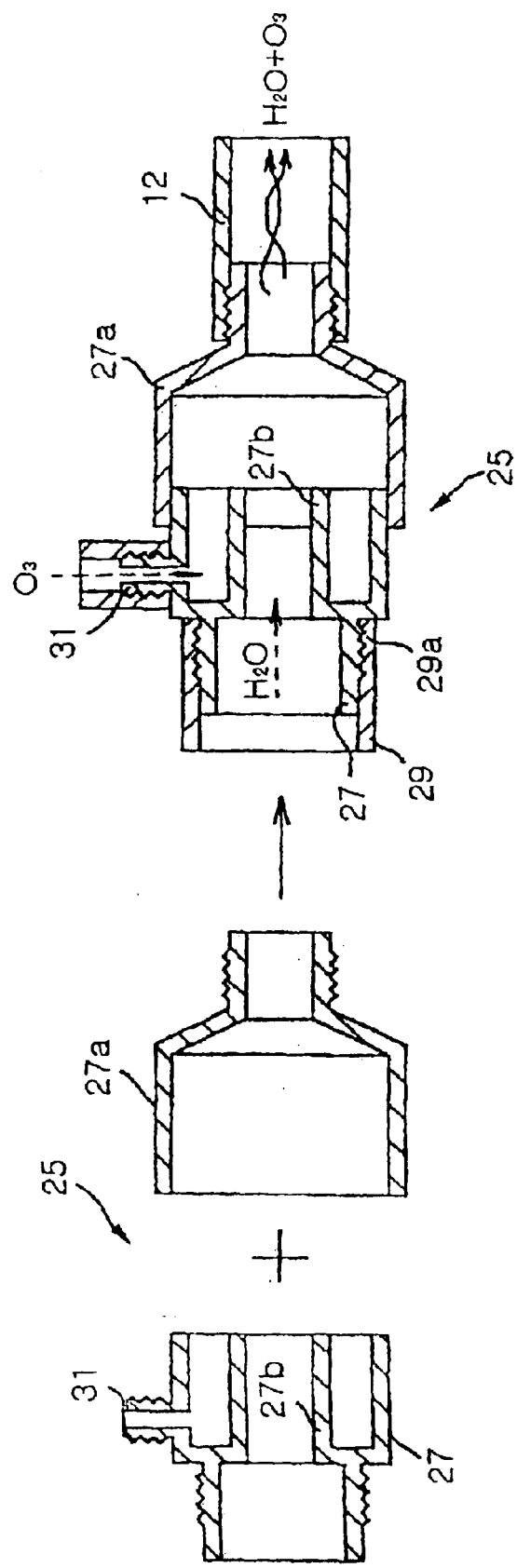
FIG. 4 is a schematic cross sectional view of an injector used in a process for producing ozone-containing water according to the invention.

Referring to the FIG. 4, there is illustrated an internal structure of the injector 25. As illustrated, the injector 25 is broken down info a hollow body 27 and a funnel type connecting pipe 27a. The hollow body 27, into one side of which an raw water inlet pipe 29 screws, is directly connected at its side point near an end 29a of the raw water inlet pipe 29 to an ozone gas inlet 31, and inserted into a body of the funnel type connecting pipe 27a. A neck of the funnel type connecting pipe 27a screws into a pump inlet 12 to be described later. A cylindrical partition 27b, which is adjacent to the raw water inlet pipe 29, is formed inside of the hollow body 27 so that the raw water introduced through the raw water inlet pipe 29 cannot directly contact the ozone gas inlet 31 and an inflow of ozone gas through the ozone gas inlet 31 may not be hindered.

In the injector 25, raw water flows at high speeds at the end 29a of the raw water inlet pipe 29 located inside the hollow body 27 due to a suction pressure from a pump inlet pipe 12 and an inflow pressure of raw water from the raw water inlet pipe 29. A pressure decrease occurs as raw water passes through the passage defined by the cylindrical patition 27b inside the hollow body 27, facilitating the introduction of the ozone gas from the ozonizer 5 into the injector 25 through the ozone gas inlet 31.

Accordingly, a bubble phase mixture of ozone gas and raw water is sucked from the injector 25 to the pump 10 through the pump inlet pipe 12, and then supplied to the compression tank 20 under a high pressure, for example 15 to 40 Kg/cm$^2$.

Returning to FIG. 3, the pressure pump 10 has a typical structure. The pressure pump 10 comprises a discharge header 36 provided with plural discharge ports 36a and 36b and a drainage port 36c for bypass. The compression tank 20 is connected with the pressure pump 10 through pipes 38 and 40 and automatic control valves 38a and 40a and, as shown in FIG. 2, one pipe 38 is connected to a first compartment 15a located in an upper side of the compressions tank 20 and the other pipe 40 is connected to a second compartment 15b located in a lower side of the compression tank 20.

Communicating through fluids with a discharge header 36 as well as with pipes 38 and 40, the drainage port 36c for bypass is connected with a drainage pipe 43 through a safety valve 43a and an automatic control valve 43b. The pressure of the safety valve 43a is established within the range of 15 to 40 Kg/cm$^2$ and defined according to the pressure of the compression tank 20, as will be described later. When the pressure of the compression tank 20 exceeds the set pressure, the safety valve is opened to discharge a mixture of ozone gas and raw water.

Figure 8:
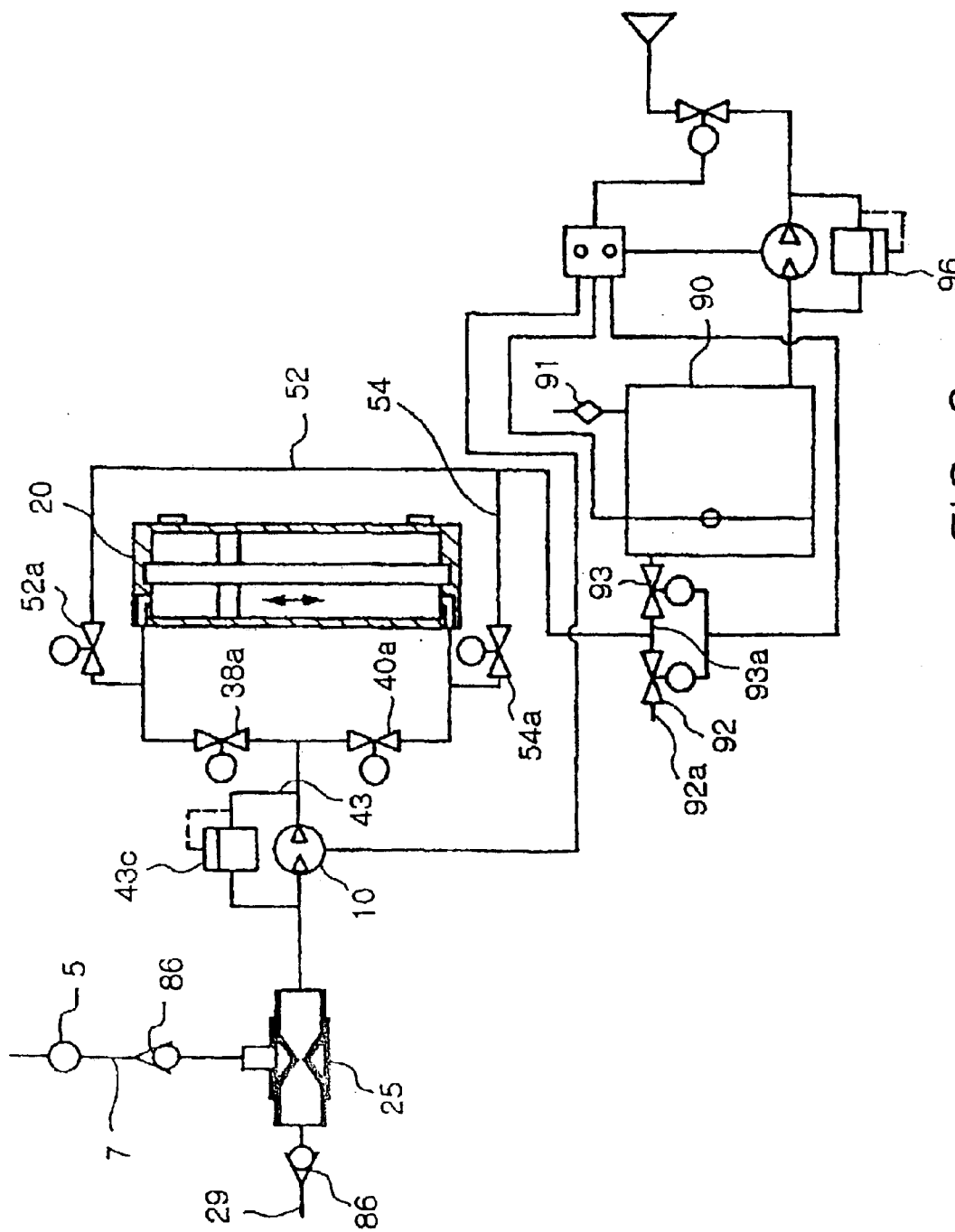
FIG. 8 illustrates a combination of a compression tank of FIG. 7, a storage tank for storing ozone-containing water, an injector, and a pump.

With reference to FIG. 8, the present invention is illustrated in accordance with another aspect. The drainage port 36c for bypass is connected with a temporary storage 43c through a drainage pipe 43, and the temporary storage 43c is connected with the pump 10 to recycle a mixture of ozone gas and raw water.

Figure 5:
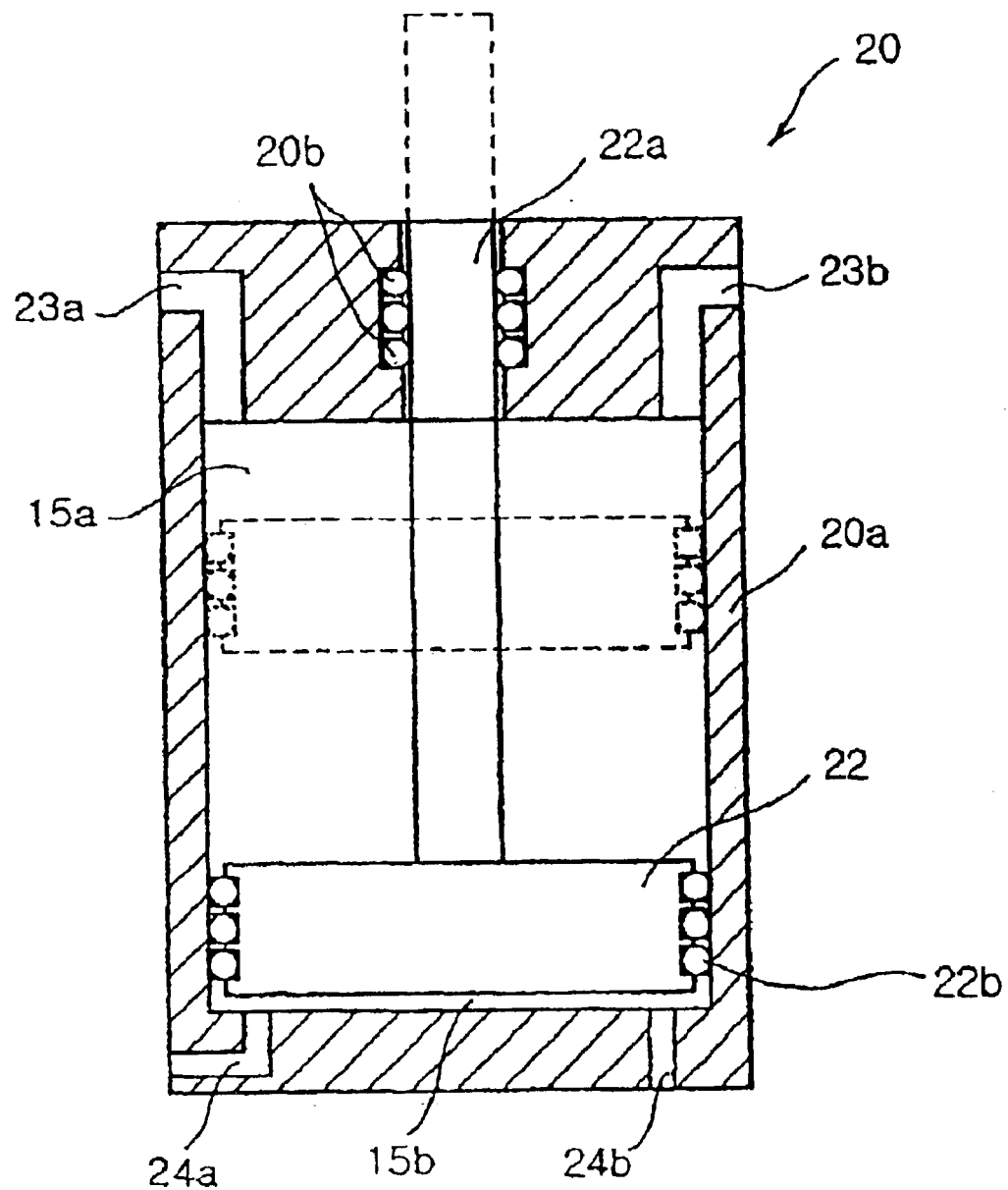
FIG. 5 is a schematic cross sectional view of a compression tank used in a process for producing ozone-containing water according to the invention.

FIG. 5 illustrates an embodiment of the compression tank 20. As shown in FIG. 5, the compression tank 20 has a hollow cylinder 20a within which a piston member 22 provided with a guide bar 22a reciprocates in a state that two compartments thus defined by the piston member 22 vary in volume with no mixing of the fluids respectively contained in the two compartments. The guide bar 22a is extended outside the compression tank 20 through the upper side of the hollow cylinder 20a. In this regard, the contact between the guide bar 22a and the upper side is tightly sealed.

The compression tank 20 is divided into a first compartment 15a and a second compartment 15b by the piston member 22 reciprocating within the hollow cylinder 20a. In the compartments 15a and 15b, inlets 23a and 24a for introducing a bubble phase mixture of ozone gas and raw water, and outlets 23b and 24b for discharging pressurized ozone-containing water are provided. In opposite verges of the upper side of the cylinder 20a are located a pair of the inlet 23a and the outlet 23b for the first compartment 15a. Likewise, a pair of the inlet 24a and the outlet 24b for the second compartment 15b are established in opposite verges of the lower side of the cylinder 20a. Through the inlets and outlets, fluids can be easily introduced into or discharged from compartments 15a and 15b.

Additionally, an outer circumference of the piston member 22, to which a plurality of sealing rings 22b are attached, makes tight contact with an inner circumference of the hollow cylinder 20a to separate a first compartment 15a from the second compartment 15b in such a way that each compartment is sealed tightly in the hollow cylinder 20a and a fluid in one compartment, which is pressurized, should not leak into the other compartment. Also, sealing rings 20b are attached to a circumference of a hole of the upper side, through which the guide bar 22a connected to the piston member 22 is disposed, in such a way that a fluid in compartments 15a and 15b should not leak to the outside during the reciprocating motion of the guide bar 22a.

Functioning to allow the piston member 22 in the cylinder 20a to be in a regular position, the guide bar 22a is marked with degrees, so that a position of the piston member 22 can be easily seen from outside. That is to say, it can be seen that when the guide bar 22a is greatly extended outwardly, the second compartment 15b located in an opposite side of the guide bar 22a is pressed, and when the guide bar 22a is slightly extended outwardly, a first compartment 15b abutted to the guide bar 22a is pressed.

Moreover, the discharge ports 23b and 24b are connected with discharge pipes 52 and 54 through automatic control valves 52a and 54a, and the valves 38a, 40a, 52a and 54a are electrically connected to a controlling means 70, which automatically controls the valves according to a predetermined program to transfer ozone gas and raw water into each compartment in turn and discharge produced ozone-containing water.

Composed of PLC (programmable logic controller) or small-sized computers, the controlling means 70 implements the continuous production of ozone-containing sterilizing water according to a predetermined program. To this end, the controlling means 70 is electrically connected with the ozonizer 5 and the pressure pump 10 to automatically control their on-off states. Also, the automatic control valve 29a located on the raw water inlet pipe 29 into the injector 25, the automatic control valve 7a located on the ozone gas inlet pipe 7 into the injector 25, the automatic control valves 38a and 40a located on the pipes 38 and 40 between the pump 10 and the compression tank 20, the automatic control valves 38a and 40a located on the pipes 38 and 40 between the pump 10 and the compression tank 20, and the automatic control valves 52a and 54a located on the discharge pipes 52 and 54 are all under the control of the controlling means 70. A valve 80 is a manual valve controlled by a user.

Ozone-containing water can be continuously produced by use of the apparatus 1 as follows. Ozone gas generated from the ozonizer 5 is continuously supplied into the injector 25 while feeding raw water. Ozone and raw water are mixed to prepare a bubble phase mixture in the injector 25, and the mixture is transferred to the compression tank 20 through the pipes 38 and 40 with the aid of the pump 40. Ozone gas can be effectively generated from the ozonizer 5 in combination with the oxygen generator 5a. That is to say, in the oxygen generator 5a, oxygen of 95% or higher purity is generated, oxygen is supplied into the ozonizer 5, after that oxygen is converted to ozone in a high voltage discharge manner in the ozonizer 5. This method enjoys advantages in that $NO_x$, is not generated and ozone is generated in large quantities.

In addition, the controlling means 70 controls valves according to the predetermined program in such a way that the valve 40a located on the pipe 40 is closed and another valve 38a located on another pipe 38 is opened, the valve 52a located on the discharge pipe 52 connected with the compression tank 20 is closed and the valve 54a located on the discharge pipe 54 connected with the compression tank 20 is opened, and so a bubble phase mixture of ozone and raw water is supplied into the first compartment 15athrough the open valve 38a located on the pipe 38 while none is supplied into the second compartment 15b.

While the first compartment 15a is pressurized, the piston member 22 descends to the bottom of a cylinder 20a, and the inside of the first compartment 15a is pressurized to a set pressure of 15 to 40 $Kg/cm^2$ when the piston member 22 descends to the bottom of a cylinder 20a. At that time, the discharge pressure of the pump 10 may be higher than the set pressure of the pump 10, and when a pressure of the inside of the first compartment 15a is higher than the set pressure of the inside of the first compartment, the safety valve 43a located on the drainage pipe 43 for bypass is opened to discharge a excessively pressurized bubble phase mixture of ozone and raw water outside, or to recycle the mixture to the pump 10 through a temporary storage 43c. Accordingly, the set pressure in the first compartment 15a is maintained for certain time. Time required to maintain the set pressure constant depends on a bactericidal activity of ozone-containing sterilizing water, and ranges, for example, from 15 seconds to 5 minutes.

In addition, ozone gas in a bubble phase mixture of ozone and raw water, which is released outside through a bypass owing to excess pressure in the first compartment 15a, is treated by use of a chemical treatment means (not shown) to not pollute the environment. The chemical treatment means according to the prior arts is not described herein.

When ozone-containing sterilizing water is produced in the first compartment 15a under 15 to 40 $Kg/cm^2$ for 30 seconds to 3 minutes, the controlling means 70 controls valves 38a, 40a, 52a and 54a, that is to say, the valves 38a and 54a are closed and the valves 40a and 52a are opened so that ozone-containing sterilizing water in the first compartment 15acan be discharged through the discharge pipe 52 and the bubble phase mixture of ozone and raw water can flow through a pipe 40 into a second compartment 15b.

When the bubble phase mixture flows into the second compartment 15b and ozone-containing water is discharged from the first compartment 15a, the piston member 22 is raised upwardly. Then the mixture in the second compartment 15b is maintained under a set pressure for a predetermined time to produce ozone-containing water in the second compartment 15b. This procedure is carried out repeatedly, so that ozone-containing water in the second compartment 15b is produced while ozone-containing water in the first compartment 15a is exhausted and vice versa.

A set pressure required for producing ozone-containing water can be accomplished by a pressure equilibrium between the first compartment 15a and the second compartment 15b.

Figure 7:
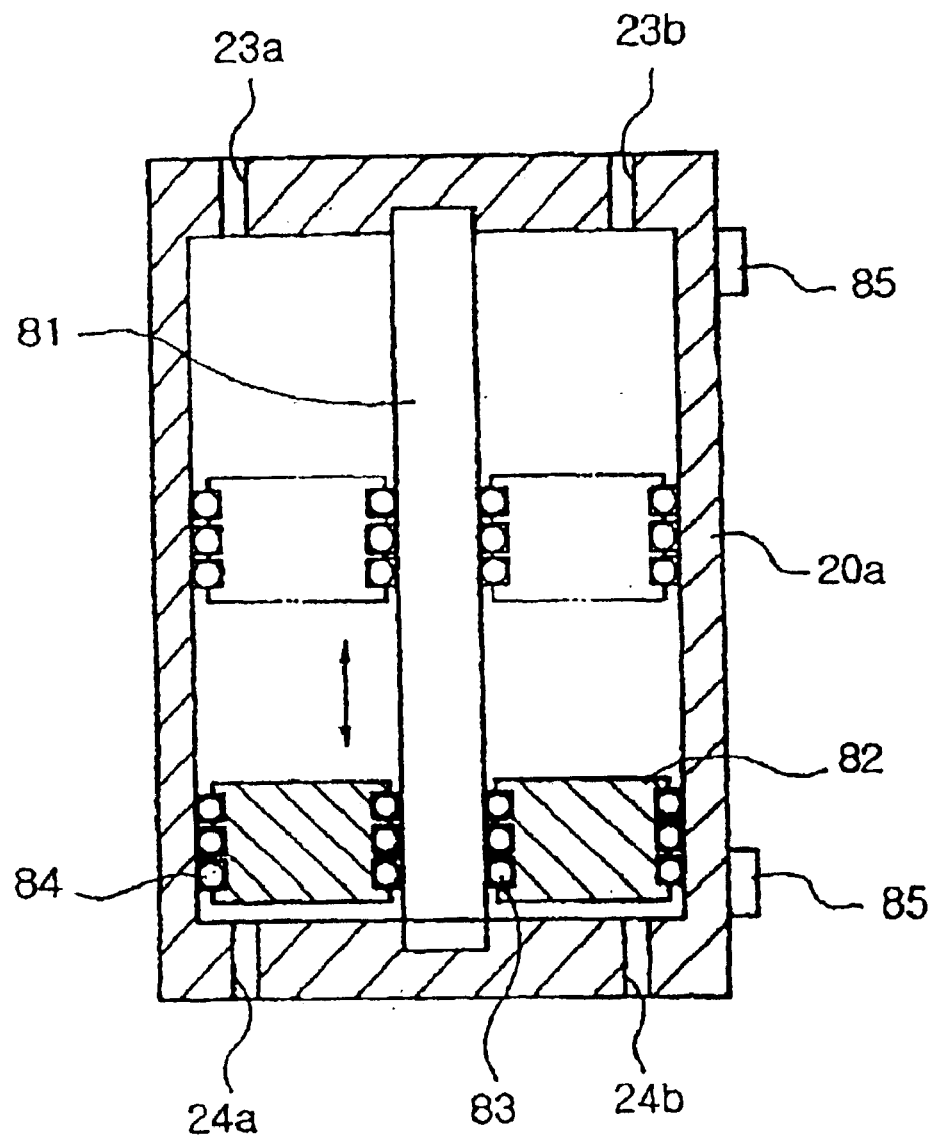
FIG. 7 is a cross sectional view of another modified compression tank used in a process for producing ozone-containing water according to the invention.

Referring to the FIG. 7 according to another embodiment of the invention, a small tank may be used instead of the compression tank according to the embodiment of FIG. 5 which is divided into the first compartment 15a and the second compartment 15b by the piston member 22 reciprocating in the compression tank.

According to the embodiment of FIG. 7, instead of the guide bar 22a of the embodiment of the FIG. 5, a guide bar 81 may be used, extending from one end side of the compression tank to the other side through the hole of the piston member.

The guide bar 81 extends from one end side of the compression tank to the other side through the hole of the piston member to support the reciprocating motion of the piston member. The piston member is provided with a plurality of sealing rings 83 and 84 at its circumference and at the inner circumference of the hole to sealably separate the compartments 15a and 15b from each other so as to prevent the leakage of a fluid pressure exerted on either of the compartments into the other compartment while the piston reciprocates along with the guide bar.

The guide bar as described above enjoys advantages in that the guide bar is not projected to outside of a compression tank 20 to reduce a space for installing the compression tank and that a fluid in the compartment does not leak to the outside of the compression tank to pressurize the mixture in the compartment more stably.

According to the embodiment of FIG. 7, the cylinder further comprises piston proximity sensors 85, which are located in upper and lower ends of the cylinder, for monitoring the position of the piston within the cylindrical compression tank and determining whether the piston is normally operated or not. The piston proximity sensors are connected with the controlling means 70 to control a pressure change according to a position change of the piston.

Raw water and ozone gas flowed into the compression tank 20 may be flowed backward owing to a back pressure of the pump 10 instead of flowing into the injector 25. Accordingly, as shown in FIG. 8, backflow prevention check valves 86 may be attached to respective positions just before raw water and ozone gas are introduced into the injector 25 so as to prevent ionizer malfunction owing to a backflow of raw water and ozone gas.

Figure 6:
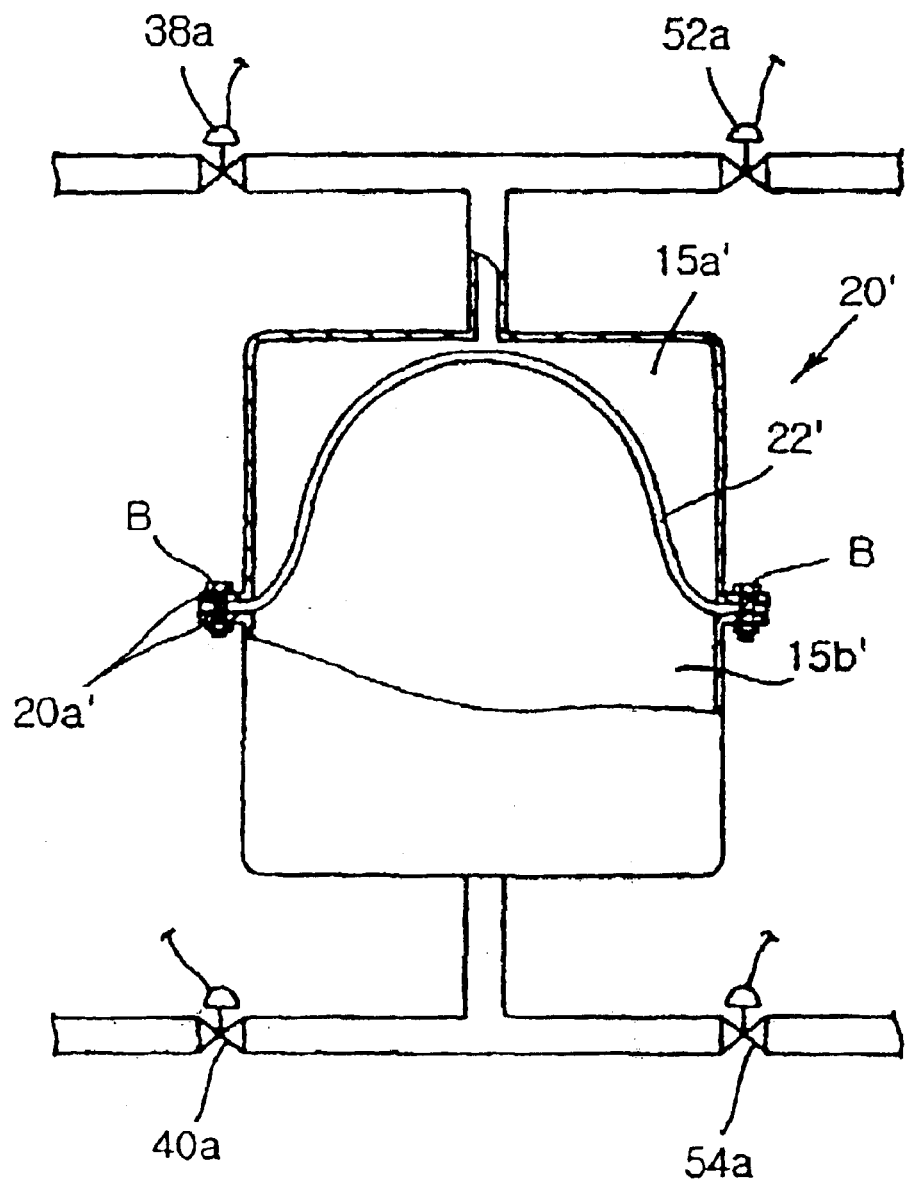
FIG. 6 is a cross sectional view of a modified compression tank used in a process for producing ozone-containing water according to the invention.

In addition, referring to the FIG. 6 according to another embodiment of compression tank of the invention, a smaller compression tank with simple structure is provided. The compression tank forms a hollow cylinder 20', and is composed of a first compartment 15a' and a second compartment 15b' divided by a flexible resilient silicone diaphragm 22' placed in the middle of the compression tank instead of a piston member 22. The flexible resilient diaphragm is the same as the piston member 22 in function. When a fluid in the second compartment 15b' is discharged and a pressure is applied into the first compartment 15a', the flexible resilient diaphragm 22' is expanded into the second compartment 15b' to maintain the first compartment 15a' at a predetermined period under a desired pressure, while when a fluid in the first compartment 15a' is discharged and a pressure is applied into the second compartment 15b', the flexible resilient diaphragm 22' is expanded into the first compartment 15a' to maintain the second compartment 15b' at a predetermined period under a desired pressure. The first compartment 15a' and the second compartment 15b' are completely separated from each other by the flexible resilient diaphragm, so that ozone-containing waters in the first and second compartments 15a' and 15b' are not mixed each other.

The compression tank 20' is horizontally divided into two parts by the diaphragm 22', which is inserted into flanges 20a' formed on the compression tank, and the diaphragm and flanges are combined with bolts B, and a contact portion of the diaphragm 22' and the compression tank 20' is sealed. The compression tank as described above has advantages of small size suitable for domestic use, and lower manufacturing cost than a compression tank 20 with the piston member 22.

With reference to FIG. 8, an ozone-containing water storage tank 90 is disclosed, which is connected with discharge pipes 52 and 54 to which valves 52a and 54a are attached.

The ozone-containing water storage tank 90 comprises a first conduit 93a connected with discharge valves 52 and 54 and a first solenoid valve 93, and a second conduit 92a connected with discharge valves 52 and 54 and a second solenoid valve 92. The first conduit 93a and the first solenoid valve 93 are connected with the ozone-containing water storage tank 90 to transfer ozone-containing water into the storage tank 90, and the second conduit 92a and the second solenoid valve 92 are connected with the discharge pipe to discharge water used in the trial run, or for washing the compression tank and pipes.

In other words, when the first solenoid valve 93 is closed and the second solenoid valve 92 is opened during the trial run of the compression tank 20, raw water passing throughout an apparatus is discharged, while when the first solenoid valve 93 is opened and the second solenoid valve 92 is closed during the steady operation of the apparatus, ozone-containing water is stored into the storage tank 90.

While ozone-containing water is stored, ozone gas is slowly decomposed to produce oxygen gas from ozone-containing water. Therefore, the storage tank should have a off-gas filter 91 for venting a small amount of gas from ozone-containing water at an upper part of the storage tank.

The storage tank 90 comprises a pump 96 for discharging ozone-containing water stored in the storage tank, thereby ozone-containing water is stably discharged.

To produce ozone-containing water according to the present invention, a regulator (not shown) may be attached to discharge pipes 52 and 54 and the ozone-containing water storage tank 90 so that ozone-containing water can be discharged under a proper pressure. It is to be understood that modifications will be apparent to those skilled in the art without departing from the spirit of the invention.

And it will be obvious to those skilled in the art that the ozonizer 5, the pump 10 and the compression tank 20 of the invention are not limited to specific structures, they may of course be applied with equal utility to modifications.

A better understanding of the present invention may be obtained in light of the following examples which are set forth to illustrate, but are not to be construed to limit the present invention.

In another embodiment of the invention, a concentration of ozone, which is contained in respective ozone-containing waters produced by the present invention, a conventional bubble type and venturi type process, and an amount of ozone released to the atmosphere were measured.

To produce ozone-containing water, an apparatus and a compression tank as shown in FIG. 2 were used, and OZ-2A220-40 manufactured by Dong Woo Co., Korea as the ozonizer was used.

In an aspect of the present invention, an apparatus and a compression tank as shown in FIG. 8 were used. The pump 10 has a recycle structure according to a volume of the compression tank. And Pacific Ozone Model manufactured by ATI Co., USA as an ozonizer 5 was used.

A concentration of ozone, which is contained in respective ozone-containing waters produced by the present invention, a conventional bubble type and venturi type process, and an amount of ozone released to the atmosphere were measured at each time.

With respect to ozone-containing water produced by the present invention, a concentration of ozone dissolved in ozone-containing water of 1.5 l and an amount of ozone released to the atmosphere were measured at each time, while concentrations of ozone contained in ozone-containing waters in a length type (volume of 5 l) and breadth type vessels (volume of 5 l) and an amount of ozone released to the atmosphere were measured at each time in bubble type process.

In venturi type process, a concentration of ozone dissolved in ozone-containing water of 8 l and an amount of ozone released to the atmosphere were measured at each time.

In FIG. 2, ozone gas of 200 ppm/hr was supplied, and a maximum amount of supplied ozone gas was 6 g/hr in FIG. 8.

A concentration of ozone dissolved in ozone-containing water was measured with the use of a dissolved ozone gas measuring instrument, Dissolved Ozone Monitor (Model A15/64) manufactured by ATI, USA, and an amount of ozone released to the atmosphere were measured with the use of a ozone gas measuring instrument, Porta Sence II (Model C16) manufactured by ATI, USA.

These measurements are described in Tables 1, 2, 3, and 4 below.

TABLE 1

Concentration of ozone in water with apparatus of FIG. 2

| Pressure | 15 sec | 30 sec | 1 min | 3 min | 5 min | 10 min | 20 min | 30 min | An odor of ozone[1] | Released ozone[2] (ppm) |
|---|---|---|---|---|---|---|---|---|---|---|
| 15 kg/cm$^2$ | 0.31 | 0.41 | 0.43 | 0.49 | 0.53 | 0.47 | 0.27 | 0.25 | None | 0.6 |
| 20 kg/cm$^2$ | 0.43 | 0.52 | 0.57 | 0.47 | 0.41 | 0.37 | 0.32 | 0.28 | None | 0.5 |
| 30 kg/cm$^2$ | 0.39 | 0.45 | 0.44 | 0.42 | 0.39 | 0.34 | 0.28 | 0.25 | None | 0.7 |
| 40 kg/cm$^2$ | 0.41 | 0.48 | 0.46 | 0.38 | 0.31 | 0.29 | 0.27 | 0.24 | None | 0.6 |

[1] An ozone gas odor of ozone-containing water
[2] An amount of ozone released from ozone-containing water to atmosphere, which is calculated as an average of 7 measurements (Volume: 1.5 l)

TABLE 2

Concentration of ozone in water with apparatus of FIG. 8

| Pressure | Time | | | | | | | | An odor of ozone[*1] | Released ozone[*2] (ppm) |
|---|---|---|---|---|---|---|---|---|---|---|
| | 15 sec | 30 sec | 1 min | 3 min | 5 min | 10 min | 20 min | 30 min | | |
| 15 kg/cm$^2$ | 1.06 | 1.54 | 2.01 | 2.4 | 2.39 | 2.01 | 1.35 | 0.98 | None | 0.04 |
| 20 kg/cm$^2$ | 1.38 | 1.45 | 2.24 | 2.68 | 2.72 | 2.49 | 1.98 | 1.02 | None | 0.01 |
| 30 kg/cm$^2$ | 1.53 | 2.01 | 3.79 | 4.21 | 4.24 | 3.15 | 2.34 | 2.04 | None | 0.009 |
| 40 kg/cm$^2$ | 1.53 | 2.14 | 3.69 | 3.98 | 4.12 | 3.12 | 2.54 | 2.12 | None | 0.01 |

[*1]An ozone gas odor of ozone-containing water
[*2]An amount of ozone released from ozone-containing water to atmosphere (Volume: 1.5 l)

TABLE 3

Concentration of ozone in water with a bubble-type apparatus

| Vessel type | Time | | | | | | | | An odor of ozone[*1] | Released ozone[*2] |
|---|---|---|---|---|---|---|---|---|---|---|
| | 15 sec | 30 sec | 1 min | 3 min | 5 min | 10 min | 20 min | 30 min | | |
| breadth type (5 l) | 0.24 | 0.25 | 0.33 | 0.49 | 0.55 | 0.55 | 0.67 | 0.62 | detected | More than 200 ppm |
| length type (8 l) | 0.31 | 0.33 | 0.45 | 0.54 | 0.62 | 0.65 | 0.71 | 0.72 | detected | More than 200 ppm |

[*1]An ozone gas odor of ozone-containing water
[*2]An amount of ozone released from ozone-containing water to atmosphere (Volume: 1.5 l)

TABLE 4

Concentration of ozone in water with a venturi-type apparatus

| Number of times | Time | | | | | | | | An odor of ozone[*1] | Released ozone[*2] |
|---|---|---|---|---|---|---|---|---|---|---|
| | 15 sec | 30 sec | 1 min | 3 min | 5 min | 10 min | 20 min | 30 min | | |
| 1 | 0.31 | 0.34 | 0.31 | 0.57 | 0.62 | 0.75 | 0.62 | 0.69 | detected | More than 200 ppm |
| 2 | 0.25 | 0.31 | 0.39 | 0.48 | 0.61 | 0.69 | 0.65 | 0.61 | detected | More than 200 ppm |

[*1]An ozone gas odor of ozone-containing water
[*2]An amount of ozone released from ozone-containing water to atmosphere (Volume: 8 l)

As apparent from the result shown in Tables 1 and 2 according to the present invention, it can be seen that a concentration of ozone in the resulting ozone-containing water is high, as well as ozone gas contained in ozone-containing water is hardly released to atmosphere (0.5 to 0.7 ppm per volume of 1.5 l) and its odor is not detected.

However, it can be seen from the result shown in Tables 3 and 4 according to the prior arts that a concentration of ozone in ozone-containing water is low, as well as ozone gas contained in ozone-containing water is released to atmosphere in large quantity and its odor can be perceived. An amount of ozone gas released to atmosphere is 150 ppm or more, which is very harmful to humans.

A process for producing ozone-containing water according to another example of the present invention is disclosed below.

To prove a bactericidal effect of ozone-containing water, 1 ml of a E-coli. broth culture was seeded into 1 l of ozone-containing water according to the present invention (maintained under 20 kg/cm$^2$ for 1 min), ozone-containing water produced according to a conventional bubble type process (breadth type, 5 min), and general tap water of Seoul city 10 times, respectively.

Bacteria were contained in the E-coli. broth culture at 1×10$^5$ cells/ml.

Samples of 1 ml extracted from each ozone-containing water, into which bacterium are seeded, was cultivated for 48 hours in a badge flask useful to cultivate bacterium. After 48 hours, growth of bacteria was observed, and the results are shown in FIGS. 1a, 1b, 1c, and 1d.

Bacteria of 4.2×10$^6$ were observed in general tap water (see, FIG. 1a) and bacteria of 4.8×10$^6$ were observed in ozone-containing water according to a conventional bubble type process, while none were observed in ozone-containing water according to the present invention. These results show that bacterium are completely sterilized in ozone-containing water according to the present invention.

Accordingly, as described above, ozone-containing sterilizing water with a bactericidal activity can be continuously produced according to the present invention, and the resulting ozone-containing sterilizing water can be applied to various fields such as sterilizing and cleaning.

INDUSTRIAL APPLICABILITY

As stated above, the present invention relates, in general, to a process for producing ozone-containing sterilizing water and apparatus used in the process, and in particular, to a continuous process for producing ozone-containing sterilizing water used for cleaning/sterilizing various foods or devices, and apparatus used in the process for producing ozone-containing sterilizing water in a simple and highly efficient manner.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A process for producing ozone-containing sterilizing water continuously, comprising the steps of:

introducing raw water and ozone gas, together, into a compression tank to produce a bubble phase mixture, said raw water being moved at a faster speed at a predetermined passage to induce a pressure drop, said ozone gas being drawn into the compression tank by the pressure drop;

charging said bubble phase mixture into any one of compartments of the compression tank, and pressurizing the mixture in the charged compartment to give ozone-containing sterilizing water, said compartments being sealably separated by a movable partition within the compression tank;

moving the partition to reduce the volume of the charged compartment to discharge the ozone-containing sterilizing water while another of said compartments is expanded in volume through being charged with said bubble phase mixture; and repeating the above steps.

2. The process according to claim 1, wherein said raw water and said ozone gas are introduced through an injector having a structure with a narrowed cross section therein, said raw water being moved at a faster speed at the narrowed cross section to induce a pressure drop, leading to the drawing of the ozone gas into the injector.

3. The process according to claim 1, wherein said bubble phase mixture is maintained in the compartment for 15 sec to 5 min under a pressure of 15 to 40 kg/cm$^2$.

4. The process according to claim 3, wherein said bubble phase mixture is maintained in the compartment for 0.5 to 1 min under a pressure of 20 to 30 kg/cm$^2$.

5. The process according to claim 1, wherein said compression tank comprises two said compartments divided by a partition.

6. The process according to claim 5, wherein said partition of the compression tank is a sealably reciprocating piston member.

7. The process according to claim 5, wherein said partition of the compression tank is a flexible resilient diaphragm placed in the middle of the compression tank.

8. An apparatus for continuously producing ozone-containing sterilizing water, comprising:

a pump for transferring a bubble phase mixture of raw water and ozone gas; and a compression tank, divided into plural number of compartments, for pressurizing the bubble phase mixture to produce ozone-containing sterilizing water, said plural compartments, in turn, receiving, pressurizing, and discharging the bubble phase mixture.

9. The apparatus according to claim 8, further comprising an injector for introducing raw water and ozone gas into the compression tank therethrough, said injector having a structure with a narrowed cross section therein, said raw water being moved at a faster speed at the narrowed cross section to induce a pressure drop, leading to the drawing of the ozone gas into the injector.

10. The apparatus according to claim 8 or 9, wherein said compression tank forms a hollow cylinder, comprising;

a piston member sealably reciprocating within the hollow cylinder; and a guide bar, extended from the piston to the outside of the compression tank through a hole established in one side of the hollow cylinder, for guiding the motion of the reciprocating piston member, whereby said hollow cylinder is divided into a first compartment and a second compartment by said piston member and the compartments vary in volume according to the motion of said piston member.

11. The apparatus according to claim 10, wherein said piston member is provided with a plurality of sealing rings at its outer circumference to sealably separate the first and the second compartment from each other so as to prevent the leakage of a fluid pressure exerted on either of the compartments into the other compartment, and said hole is provided with a plurality of sealing rings at its wall to prevent the leakage of a fluid pressure of the compartment to the outside therethrough during the reciprocating motion of said guide bar.

12. The apparatus according to claim 11, wherein said guide bar allows the piston member to be at a regular position in the hollow cylinder, and is marked on its one side with degrees so that the position of the piston member can be easily found from outside.

13. The apparatus according to claim 10, wherein each of the two compartments has an inlet for introducing a bubble phase mixture of raw water and ozone gas and an outlet for discharging pressurized ozone-containing sterilizing water, and a pair of said inlet and outlet are formed in each of the upper verge and lower verge of the cylinder, respectively.

14. The apparatus according to claim 8, wherein said plural compartments are defined by a flexible resilient diaphragm placed in the middle of the compression tank, consisting of a first compartment and a second compartment, said flexible resilient diaphragm being operated in such a way that the flexible resilient diaphragm is expanded toward the second compartment by increasing the pressure of the first compartment to a predetermined value and maintaining the pressure for a predetermined period of time to discharge a fluid from the second compartment, and toward the first compartment by increasing the pressure of the second compartment to a predetermined value and maintaining the pressure for a predetermined period of time to discharge a fluid from the first compartment.

15. An apparatus for continuously producing ozone-containing sterilizing water, comprising:

a pump for transferring a bubble phase mixture of raw water and ozone gas; and a cylindrical compression tank, divided into a plural number of compartments by a donut-type piston member having a hole at the center, for pressurizing the bubble phase mixture to produce ozone-containing sterilizing water, said piston member being provided with a plurality of sealing rings at its circumference and at the inner circumference of the hole to sealably separate the plural compartments from each other so as to prevent the leakage of a fluid pressure exerted on either of the compartments into the other compartment, and moving, along a guide bar, in such a reciprocating manner within the compression tank as to pressurize the bubble phase mixture in the plural compartments, in turn, said guide bar extending from one end side of the compression tank to the other side through the hole of the piston member to support the reciprocating motion of the piston member.

16. The apparatus according to claim 15, further comprising an injector for introducing raw water and ozone gas into the compression tank therethrough, said injector having a structure with a narrowed cross section therein, said raw water being moved at a faster speed at the narrowed cross section to induce a pressure drop, leading to the drawing of the ozone gas into the injector.

17. The apparatus according to claim 15, further comprising a piston proximity sensor for monitoring the position of the piston within the cylindrical compression tank and determining whether the piston is normally operated or not.

18. The apparatus according to claim 15, wherein each of the two compartments has an inlet for introducing a bubble phase mixture of raw water and ozone gas and an outlet for discharging pressurized ozone-containing sterilizing water, and a pair of said inlet and outlet are formed in each of the upper verge and lower verge of the cylinder, respectively.

19. The apparatus according to claim 16, wherein a backflow prevention check valve is provided just before the inlets for introducing raw water and ozone gas into the injector, each, to prevent the raw water and ozone gas from flowing backward by a back pressure of the pump.

20. An apparatus for continuously producing ozone-containing sterilizing water, comprising:

an injector for mixing raw water with ozone gas to give a bubble phase mixture of raw water and ozone gas, said injector having a structure with a narrowed cross section therein, said raw water being moved at a faster speed at the narrowed cross section to induce a pressure drop, leading to the drawing of the ozone gas into the injector;

a pump for transferring a bubble phase mixture of said raw water and ozone gas; and a compression tank, formed into a hollow cylinder, for pressurizing the bubble phase mixture to produce ozone-containing sterilizing water, said compression tank comprising;

a piston member sealably reciprocating within the hollow cylinder; and a guide bar, extended from the piston to the outside of the compression tank through a hole established in one side of the hollow cylinder, for guiding the motion of the reciprocating piston member, whereby said hollow cylinder is divided into a first compartment and a second compartment by said piston member and the compartments vary in volume, in turn, to pressurize the bubble phase mixture according to the reciprocating motion of said piston member.

21. The apparatus according to claim 20, further comprising a piston proximity sensor for monitoring the position of the piston within the cylindrical compression tank and determining whether the piston is normally operated or not.

22. The apparatus according to claim 20, wherein a backflow prevention check valve is provided just before inlets for introducing raw water and ozone gas into the injector, each, to prevent the raw water and ozone gas from flowing backward by a back pressure of the pump.

23. The apparatus according to claim 20, wherein the first and the second compartment are individually provided with an inlet for introducing the bubble phase mixture of ozone gas and raw water thereinto and an outlet for discharging the pressurized ozone-containing sterilizing water therefrom, and a pair of said inlet and outlet are formed in each of the upper verge and lower verge of the cylinder, respectively, and the apparatus further comprises:

a storage tank for storing the ozone-containing sterilizing water, provided with an off-gas filter for venting the gas generated during the storage of the ozone-containing sterilizing in the storage tank;

a first conduit, provided with a first solenoid valve, for connecting each outlet with said storage tank; and a second conduit, provided with a second solenoid valve, for connecting each outlet with a drainage pipe, said first and second solenoid valve functioning in such a way that, during the trial run of said apparatus, said second solenoid valve is opened with closing of said first solenoid valve so as to drain unpressurized raw water from the compression tank and, during the steady operation of said apparatus, said first solenoid valve is opened with closing of said second solenoid valve so as to discharge ozone-containing sterilizing water into the storage tank.

24. The apparatus according to claim 20, wherein said ozone gas is generated by an ozonizer using oxygen provided from an oxygen generator.

25. An apparatus for continuously producing ozone-containing sterilizing water, comprising:

an injector for mixing raw water with ozone gas to give a bubble phase mixture of raw water and ozone gas, said injector having a structure with a narrowed cross section therein, said raw water being moved at a faster speed at the narrowed cross section to induce a pressure drop, leading to the drawing of the ozone gas into the injector;

pump for transferring a bubble phase mixture of said raw water and ozone gas; and a compression tank, formed into a hollow cylinder, for pressurizing the bubble phase mixture to produce ozone-containing sterilizing water, said hollow cylinder being divided into a first and a second compartment by a flexible resilient diaphragm placed in the middle of the compression tank, said flexible resilient diaphragm being operated in such a way that the flexible resilient diaphragm is expanded toward the second compartment by increasing the pressure of the first compartment to a predetermined value and maintaining the pressure for a predetermined period of time to discharge a fluid from the second compartment, and toward the first compartment by increasing the pressure of the second compartment to a predetermined value and maintaining the pressure for a predetermined period of time to discharge a fluid from the first compartment.

26. The apparatus according to claim 25, wherein the first and the second compartment are individually provided with an inlet for introducing the bubble phase mixture of ozone gas and raw water thereinto and an outlet for discharging the pressurized ozone-containing sterilizing water therefrom, and a pair of said inlet and outlet are formed in each of the upper verge and lower verge of the cylinder, respectively, and the apparatus further comprises:

- a storage tank for storing the ozone-containing sterilizing water, provided with an off-gas filter for venting the gas generated during the storage of the ozone-containing sterilizing in the storage tank;
- a first conduit, provided with a first solenoid valve, for connecting each outlet with said storage tank; and
- a second conduit, provided with a second solenoid valve, for connecting each outlet with a drainage pipe, said first and second solenoid valve functioning in such a way that, during the trial run of said apparatus, said second solenoid valve is opened with closing of said first solenoid valve so as to drain unpressurized raw water from the compression tank and, during the steady operation of said apparatus, said first solenoid valve is opened with closing of said second solenoid valve so as to discharge ozone-containing sterilizing water into the storage tank.

27. The apparatus according to claim 25, wherein said ozone gas is generated by an ozonizer using oxygen provided from an oxygen generator.

* * * * *